United States Patent [19]

Sekizawa et al.

[11] 4,229,448
[45] Oct. 21, 1980

[54] 5-SUBSTITUTED PICOLINIC ACID DERIVATIVES AND AN ANTI-HYPERTENSIVE COMPOSITION CONTAINING THE SAME

[75] Inventors: Yasuharu Sekizawa, Tokyo; Takashi Tsuruoka; Mitsugu Hachisu, both of Kawasaki; Masaji Sezaki, Tokyo; Masashi Miyamoto, Tokyo; Uichi Shibata, Tokyo; Kazuko Mizutani, Yokohama; Shigeharu Inouye, Yokohama; Takemi Koeda, Yokohama; Keizo Shimomura, Tokyo; Taro Niida, Yokohama, all of Japan

[73] Assignee: Meuji Seika Kaisha Ltd., Tokyo, Japan

[21] Appl. No.: 23,504

[22] Filed: Mar. 23, 1979

[30] Foreign Application Priority Data

Mar. 24, 1978 [JP] Japan .................... 53-32967
Jul. 4, 1978 [JP] Japan .................... 53-80485

[51] Int. Cl.³ .............. A61K 31/455; C07D 213/79
[52] U.S. Cl. ....................... 424/245; 424/266; 546/5; 546/298
[58] Field of Search ............ 424/245, 266; 546/298, 546/5

[56] References Cited

U.S. PATENT DOCUMENTS 3,983,126 9/1976 Dufour ..................... 546/298

FOREIGN PATENT DOCUMENTS 2138188 1/1973 France .................... 546/298

OTHER PUBLICATIONS

Maeda et al., Chemical Abstracts, vol. 81 (1974) 135,964k.
Endo et al., Chemical Abstracts, vol. 54 (1960) 24,705d.

*Primary Examiner*—Richard Raymond
*Attorney, Agent, or Firm*—Sughrue, Rothwell, Mion, Zinn and Macpeak

[57] ABSTRACT

5-Substituted picolinic acid derivatives represented by the formula (I):

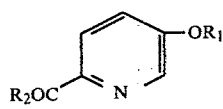

(I)

wherein $R_1$ represents a straight or branched chain halogen-substituted alkyl group having 2 to 6 carbon atoms or a substituted phenyl group having the formula

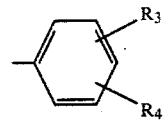

wherein $R_3$ and $R_4$, which may be the same or different, each represents a hydrogen atom, a halogen atom, a lower alkyl group, a lower alkoxy group, a nitro group, an amino group, an N-alkyl-substituted amino group, an acylamino group, an acetyl group, an acyloxy group, a hydroxy group or a halogen-substituted alkyl group or $R_3$ and $R_4$, when taken together, represent a polymethylene chain; and $R_2$ represents an —OM group wherein M represents a hydrogen, sodium, potassium, calcium, aluminium or magnesium atom, a straight or branched chain or cyclic alkoxy group having 1 to 6 carbon atoms, an aminoalkoxy group, a phenoxy group, a substituted phenoxy group, a 5-indanyloxy group, an acyloxyalkyloxy group having the formula

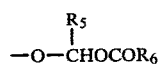

wherein $R_5$ represents a hydrogen atom or a methyl group and $R_6$ represents a lower alkyl group having 1 to 6 carbon atoms, a phenyl group or a substituted phenyl group, or an amino group represented by the formula

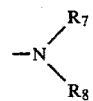

wherein $R_7$ and $R_8$, which may be the same or different, each represents a hydrogen atom, a lower alkyl group, or a phenyl group which are useful as anti-hypertensive agents, a process for preparing the above 5-substituted picolinic acid derivatives, and anti-hypertensive compositions containing the same.

10 Claims, No Drawings

5-SUBSTITUTED PICOLINIC ACID DERIVATIVES AND AN ANTI-HYPERTENSIVE COMPOSITION CONTAINING THE SAME

BACKGROUND OF THE INVENTION

1. Field of the Invention

This invention relates to new and useful 5-substituted picolinic acids and salts thereof, 5-substituted picolinic esters and 5-substituted picolinic acid amides, to a process for preparing the same, and to pharmaceutical compositions containing the same.

2. Description of the Prior Art

It is known that hypertension often includes apoplexy, heart trouble, etc., which necessitates extensive research for new and useful anti-hypertensives.

Fusaric acid (5-n-butylpicolinic acid) is known to be useful as an anti-hypertensive agent as disclosed in *Jap. J. Pharmacol.*, Vol. 25, 188 (1975), however, fusaric acid has a butyl group at the 5-position of the picolinic acid moiety and has a low $LD_{50}$ value. As a result, an improved anti-hypertensive agent is desired.

British Pat. No. 1,502,055 discloses that 3-substituted-2(1H)-pyridone-6-carboxylic acid can be used as an anti-hypertensive agent but the anti-hypertensive activity (i.e., maximum depression in blood pressure) thereof is poor and an improvement is desired.

The inventors have already synthesized 5-alkoxypicolinic acids and evaluated them as anti-hypertensive agents as reported in Japanese Patent Application No. 116641/1976 (corresponding to U.S. patent application Ser. No. 838,180, filed on Sept. 30, 1977). It has now been found that the compounds of the present invention exhibit anti-hypertensive activity equal or superior to 5-alkoxypicolinic acids of the Japanese patent application No. 116641/1976 and have lower toxicity than 5-alkoxypicolinic acids of the Japanese Patent Application No. 116641/1976 and, therefore, the compounds of the present invention are useful compounds for the treatment of hypertension.

SUMMARY OF THE INVENTION

It is a principal object of the present invention to provide a novel group of anti-hypertensive agents.

It is another object of the present invention to provide a novel group of anti-hypertensive agents which are less toxic than 5-alkoxypicolinic acids but equal to or superior to 5-alkoxypicolinic acids in their anti-hypertensive activity.

Still another object of the present invention is to provide novel processes for producing these anti-hypertensive agents.

Accordingly, the present invention provides 5-substituted picolinic acid derivatives represented by the formula (I):

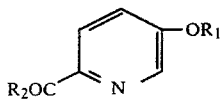
(I)

wherein $R_1$ represents a straight or branched chain halogen-substituted alkyl group having 2 to 6 carbon atoms or a substituted phenyl group of the formula

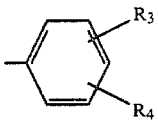

wherein $R_3$ and $R_4$, which may be the same or different, each represents a hydrogen atom, a halogen atom, a lower alkyl group, a lower alkoxy group, a nitro group, an amino group, an N-alkyl-substituted amino group, an acylamino group, an acetyl group, an acyloxy group, a hydroxyl group or a halogen-substituted alkyl group, or $R_3$ and $R_4$, when taken together, represent a polymethylene chain; and $R_2$ represents an —OM group wherein M represents a hydrogen atom, a sodium atom, a potassium atom, a calcium atom, an aluminium atom or a magnesium atom, a straight or branched chain or cyclic alkoxy group having 1 to 6 carbon atoms, an aminoalkoxy group, a phenoxy group, a 5-indanyloxy group, an acyloxyalkyloxy group having the formula

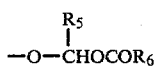

wherein $R_5$ represents a hydrogen atom or a methyl group and $R_6$ represents a lower alkyl group having 1 to 6 carbon atoms, a phenyl group or a substituted phenyl group, or an amino group represented by the formula

wherein $R_7$ and $R_8$, which may be the same or different, each represents a hydrogen atom, a lower alkyl group or a phenyl group.

DETAILED DESCRIPTION OF THE INVENTION

In the formula (I), $R_1$ represents a straight or branched chain halogen-substituted alkyl group having 2 to 6 carbon atoms (such as a 4-chlorobutyl group, a 4-bromobutyl group, a 3-chloropropyl group, a 5,5,5-trifluoropentyl group, a 4,4,4-trifluorobutyl group, a 3,4-dibromobutyl group, a 5-chloro-3-methyl-pentyl group, etc.); or a substituted phenyl group having the formula

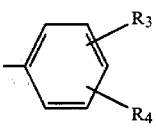

wherein $R_3$ and $R_4$, which may be the same or different, each represents a hydrogen atom, a halogen atom (such as chlorine, bromine, fluorine, etc.), a lower alkyl group having 1 to 3 carbon atoms (such as a methyl group, an ethyl group, a propyl group, etc.), a lower alkoxy group having 1 to 3 carbon atoms (such as a methoxy group, an ethoxy group, a propoxy group, etc.), a nitro group, an amino group, an N-alkyl-substituted amino group wherein the alkyl moiety has 1 to 3 carbon atoms (such as a dimethylamino group, a diethylamino group, etc.), an acylamino group having 2 to 4 carbon atoms (such as an acetamido group, a propionylamino group, etc.), an acetyl group, an acyloxy group having 2 to 4 carbon atoms (such as an acetoxy group, a propionyloxy group, etc.), a hydroxy group or a halogen-substituted alkyl group having 1 to 3 carbon atoms (such as a trifluoromethyl group, etc.), or $R_3$ and $R_4$, when taken together, represent a polymethylene chain having 3 to 5 carbon atoms (such as trimethylene, etc.).

$R_2$ represents an —OM group wherein M represents a hydrogen atom, a sodium atom, a potassium atom, a calcium atom, an aluminium atom or a magnesium atom; a straight or branched chain or cyclic alkoxy group having 1 to 6 carbon atoms (such as a methoxy group, an ethoxy group, a propoxy group, an isobutoxy group, a cyclohexyloxy group, etc.); an aminoalkoxy group having 2 to 5 carbon atoms (such as a dimethylaminoethyloxy group, etc.); a phenoxy group (including a phenoxy group substituted as illustrated below for the phenyl group); a 5-indanyloxy group; an acyloxyalkyloxy group having the formula

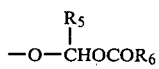

wherein $R_5$ represents a hydrogen atom or a methyl group and $R_6$ represents a lower alkyl group having 1 to 6 carbon atoms (such as a methyl group, an ethyl group, a propyl group, an isobutyl group, a t-butyl group, etc.), a phenyl group or a substituted phenyl group wherein the substituent includes an alkyl group having 1 to 3 carbon atoms and an alkoxy group having 1 to 3 carbon atoms (such as a p-tolyl group, a p-methoxyphenyl group, a 3,4,5-trimethoxyphenyl group, etc.); or an amino group represented by the formula

wherein $R_7$ and $R_8$, which may be the same or different, each represents a hydrogen atom, a lower alkyl group having 1 to 4 carbon atoms (such as a methyl group, an ethyl group, etc.), or a phenyl group.

Compounds represented by the formula (II-a):

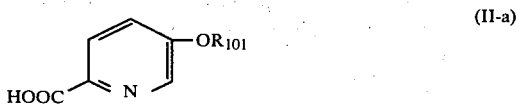

wherein $R_{101}$ represents a straight or branched chain halogen-substituted alkyl group having 2 to 6 carbon atoms, can be prepared by reacting a compound represented by the formula (IV):

wherein $R_9$ represents a methyl group or a hydroxymethyl group, with a halide represented by the formula (V):

wherein $R_{101}$ is as dfined above and X represents a halogen atom, in an organic solvent such as dimethylformamide, dimethyl sulfoxide, dimethylacetamide and the like in the presence of an inorganic base such as potassium hydroxide, sodium hydroxide, potassium carbonate, sodium carbonate, sodium hydrogencarbonate and the like or an organic base such as triethylamine, N,N-dimethylaniline and the like to obtain a compound represented by the formula (VI):

wherein $R_9$ and $R_{101}$ are as defined above.

This substitution reaction takes place selectively at the 5-position hydroxy group, and no reaction of the —$CH_2OH$ group or by-production of pyridinium salts is observed under the conditions of the invention. The reaction easily proceeds at a temperature ranging from about 30° to 100° C. and is completed in a relatively short time such as about 1 to 20 hours.

The compounds of the formula (II-a) according to this invention can be prepared by oxidizing the intermediate of the formula (VI) as described above using an oxidizing agent such as potassium permanganate, chromic anhydride, selenium dioxide, nitric acid, potassium bichromate and the like in a solvent such as acetone, dioxane, pyridine, hydrous acetone, hydrous t-butanol, sulfuric acid and the like. Any impurities by-produced during the reaction can easily be removed by solvent extraction, precipitation, crystallization or a like operation. Reaction conditions for the oxidation vary with kind of the oxidizing agent used and $R_9$ group in the compound of the formula (VI). When $R_9$ group is hydroxymethyl group, the reaction conditions for the oxidation are generally mild. For example, when the compound of the formula (VI) having hydroxymethyl group as the $R_9$ group is oxidized with potassium permanganate, about 1 to 2 mols of potassium permanganate per mol of the compound of the formula (VI) is used and the reaction time and reaction temperature are about 5° to 20° C. and about 2 to 20 hours, respectively. In the case of oxidizing the compound of the formula (VI) having a methyl group as the $R_9$ group with potassium permanganate, about 2 to 4 mols of potassium permanganate per mol of the compound of the formula (VI) are needed at the reaction temperature of about 80° to 100° C. and for the reaction time of about 4 to 10 hours. In a case of oxidizing the compound of the formula (VI) having a methyl group as the $R_9$ group with chromic anhydride, about 2.5 to 3.5 mols of chromic anhydride per mol of the compound of the formula (VI) is used in the presence of sulfuric acid at the reaction temperature of about 30° to 70° C. for the reaction time of about 4 to 10 hours. When selenium dioxide is used as an oxidizing agent, the oxidation reaction is carried out in the presence of pyridine in an amount of about 1.8 to 2.5 mols of selenium dioxide per mol of the compound of the formula (VI) at reaction temperature of about 100° to 120° C. for reaction time of about 5 to 10 hours.

Compounds represented by the formula (II-f):

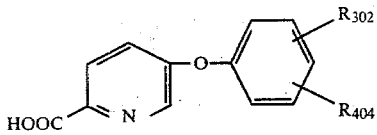

wherein $R_{302}$ and $R_{404}$, which may be the same or different, each represents a hydrogen atom, a halogen atom, a lower alkyl group, a lower alkoxy group, a nitro group, an amino group, an N-alkyl-substituted amino group, an acylamino group, an acetyl group, or a halogen-substituted alkyl group, or $R_{302}$ and $R_{404}$, when taken together, represent a polymethylene chain can be obtained by reacting the compound of the formula (IV) or a metal salt thereof such as a potassium salt, a sodium salt, etc., with a substituted halobenzene derivative represented by the formula (VII-a):

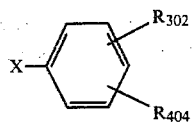

wherein $R_{302}$ and $R_{404}$ are as defined above and X is a halogen atom, in an organic solvent such as dimethylformamide, dimethylacetamide, pyridine, collidine and the like preferably in the presence of a catalyst such as a copper powder, copper oxide, copper chloride and the like to obtain a compound represented by the formula (VIII-b):

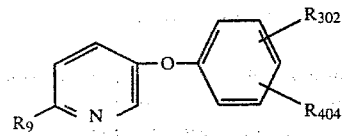

wherein $R_9$, $R_{302}$ and $R_{404}$ are as defined above. Of the compounds of the formula (VII-a), those wherein at least one of $R_{302}$ and $R_{404}$ is a nitro group and the nitro group is positioned at ortho- or para-position of the halogen X may be prepared under mild conditions such as at a reaction temperature of about 50° to 100° C. in a reaction time of about 10 to 15 hours without catalyst.

The halobenzene derivative of the formula (VII-a) is used in an amount of about 0.9 to 1.2 mols per mol of the compound of the formula (IV). The reaction requires a higher temperature than in the preparation of the compounds of the formula (II-a) generally ranging from about 90° to 180° C. and takes a relatively long reaction time to complete such as about 8 to 30 hours. The reaction is usually carried out in a nitrogen stream in order to prevent side reactions such as oxidation and polymerization. In the case of using copper powder as the catalyst, about 5 to 15 wt% of copper powder per weight of the compound of the formula (IV) is used at a reaction temperature of about 100° to 150° C. for a reaction time of about 10 to 20 hours. In the case of using copper oxide or copper chloride as the catalyst, about 0.2 to 0.3 mol of copper oxide or copper chloride per mol of the compound of the formula (IV) is used at a reaction temperature of about 130° to 160° C. for a reaction time of about 10 to 20 hours. In both cases above, the reaction is carried out in a nitrogen gas stream.

Then, the compound of the formula (VIII-b) is oxidized in a solvent such as acetone, dioxane, hydrous acetone, pyridine, water, hydrous t-butanol, sulfuric acid and the like using an oxidizing agent such as potassium permanganate, selenium dioxide, chromic anhydride, nitric acid, potassium bichromate and the like, thereby to obtain the compound of the formula (II-f). The oxidation conditions for this reaction are the same as those for the oxidation of the compound of the formula (VI) obtained above.

Of the compounds of the formula (VIII-b), those wherein at least one of $R_{302}$ and $R_{404}$ is a nitro group may be prepared under the conditions employed in the preparation of the compounds of the formula (II-a) since the reaction reagent of the formula (VII-a) is active.

Among the compounds of the formula (II-f), those wherein at least one of $R_{302}$ and $R_{404}$ is a nitro group can be subjected to reduction using tin or stannic chloride in hydrochloric acid or an iron powder in hydrochloric acid or catalytic reduction in an alcohol, a dioxane, a hydrous alcohol, an ammoniacal alcohol or an ammoniacal hydrous alcohol in the presence of a catalyst such as platinum oxide, palladium, Raney nickel and the like to obtain a compound represented by the formula (II-h) having at least one amino group on the phenoxy moiety:

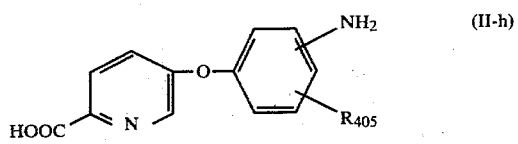

wherein $R_{405}$ represents a hydrogen atom, a halogen atom, a lower alkyl group, a lower alkoxy group, an amino group, an N-alkyl-substituted amino group, an acylamino group, an acetyl group or a halogen-substituted alkyl group. In the case of using stannic chloride or iron powder as the reducing agent, about 3 mols of stannic chloride or 2.5 to 5 atoms of iron powder per mol of the compound of the formula (II-f) is used under acidic conditions, generally in hydrochloric acid, at a reaction temperature of room temperature (about 15° C. to about 30° C.) to about 70° C. for a reaction time of about 5 to 20 hours. In the case of catalytic reduction, the catalyst (such as platinum oxide, palladium, Raney nickel) is used in an amount of about 5 to 10 wt% based on the compound of the formula (II-f) and the catalytic reduction is carried out in neutral or alkaline condition at room temperature (about 15° C. to about 30° C.) and atmospheric pressure for a reaction time of about 2 to 5 hours.

When the above-described catalytic reduction is carried out in an acid anhydride or a mixed solvent of an acid anhydride and an organic acid constituting the same, a compound represented by the formula (II-i) containing an acylamino substituent:

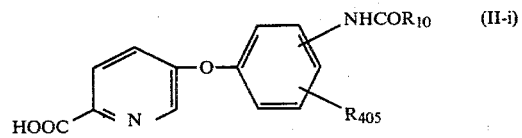

wherein $R_{10}$ represents a lower alkyl group and $R_{405}$ is the same as defined above is obtained.

The compounds of the formula (II-h) may also be easily prepared by hydrolyzing the compound of the formula (II-i) as described above with an acid or an alkali, followed by deacylation.

The compound of the formula (II-h) as obtained above is dissolved in an aqueous solution containing a mineral acid such as hydrochloric acid, sulfuric acid, hydrobromic acid and the like, and sodium nitrite is added thereto under ice-cooling to form a diazonium salt of the compound (II-h). The diazotization is usually carried out in the presence of acid such as hydrochloric acid, sulfuric acid or hydrobromic acid using sodium nitrite ($NaNO_2$) in an amount of about 1 to 1.2 mols per mol of the compound of the formula (II-h) at a reaction temperature of 0° to 10° C. The resulting diazonium salt can be chlorinated or brominated by treating with cuprous chloride/hydrochloric acid or cuprous bromide/hydrobromic acid, iodinated by adding potassium iodide or fluorinated by adding fluoroboric acid and heating the resulting diazonium fluoroborate, thereby to obtain a compound represented by the formula (II-j) having at least one halogen atom on the phenoxy moiety:

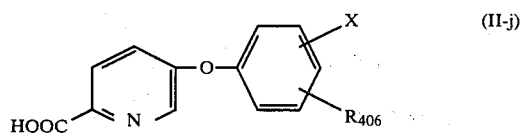

wherein X represents a halogen atom and $R_{406}$ represents a hydrogen atom, a halogen atom, a lower alkyl group, a lower alkoxy group, an N-alkyl-substituted amino group, an acylamino group, an acetyl group or a halogen-substituted alkyl group.

Compounds represented by the formula (II-k) having at least one hydroxy group on the phenoxy ring:

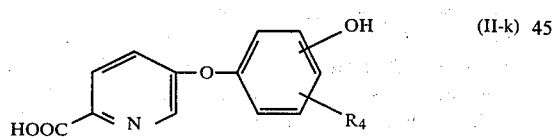

wherein $R_4$ is the same as defined above, can easily be prepared by dealkoxylation of the compound of the formula (II-f) in a hydrohalogenic acid under heating or by treating the diazonium salt of the compound (II-h) with an aqueous dilute acid.

Compounds represented by the formula (VIII):

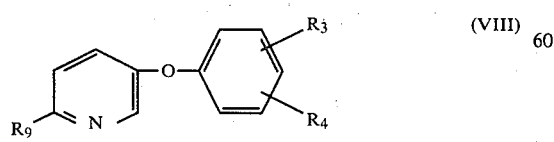

wherein $R_3$, $R_4$ and $R_9$ are the same as defined above, which are intermediates for the compounds represented by the formula (II-b):

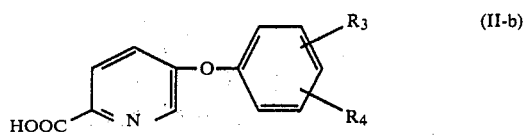

wherein $R_3$ and $R_4$ are the same as defined above, may also be obtained by the following process:

That is, the compounds of the formula (II-b) can be prepared by reacting a compound represented by the formula (IX):

wherein X represents a halogen atom and $R_9$ is as defined above, with a substituted phenol represented by the formula (X-a):

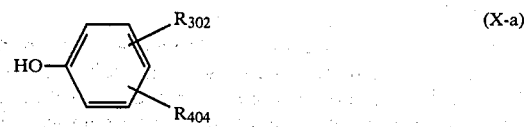

wherein $R_{302}$ and $R_{404}$ are the same as defined above. The reaction proceeds under the same conditions as described in the condensation reaction between the compound of the formula (IV) and the compound of the formula (VII-a).

The 5-substituted picolinic acids as above obtained can easily be converted to pharmaceutically acceptable salts thereof such as calcium salts, sodium salts, aluminium salts, magnesium salts and potassium salts.

This invention provides a process for preparing a 5-substituted picolinic acid ester or amide represented by the formula (III):

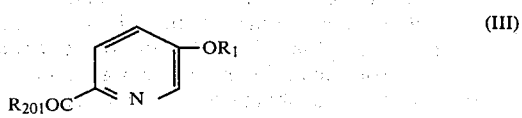

wherein $R_1$ represents a straight or branched chain halogen-substituted alkyl group having 2 to 6 carbon atoms or a substituted phenyl group represented by the formula

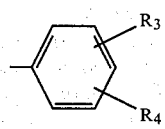

wherein $R_3$ and $R_4$ are defined as above; and $R_{201}$ represents a straight or branched chain or cyclic alkoxy group having 1 to 6 carbon atoms, an aminoalkoxy group, a phenoxy group, a substituted phenoxy group, a 5-indanyloxy group, an acyloxyalkyloxy group represented by the formula

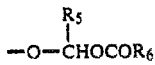

wherein $R_5$ and $R_6$ are defined as above, or an amino group represented by the formula

wherein $R_7$ and $R_8$ are defined as above, which comprises:

(i) reacting a 5-substituted picolinic acid or a metal salt thereof represented by the formula (II-g):

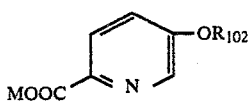
(II-g)

wherein $R_{102}$ represents a straight or branched chain halogen-substituted alkyl group (containing a halogen atom such as chlorine, bromine, iodine and fluorine) or a substituted phenyl group represented by the formula

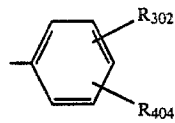

wherein $R_{302}$ and $R_{404}$ are defined as above; and M represents a hydrogen atom or a metal atom (such as sodium, potassium, calcium, aluminium and magnesium), with one of an aliphatic alcohol having 1 to 6 carbon atoms, 5-indanol, phenol, substituted phenols and amines represented by the formula (XI):

(XI)

wherein $R_7$ and $R_8$ are defined as above, in the presence of an acid catalyst or a condensation agent; or (ii) reacting a 5-substituted picolinic acid or a metal salt of the formula (II-g) with an acyloxyalkyl halide represented by the formula (XII):

(XII)

wherein $R_5$ and $R_6$ are as defined above, and X represents a halogen atom, in the presence of a base.

More specifically, of the compounds having the formula (III) according to the present invention, lower alkyl esters such as methyl, ethyl, propyl and isobutyl esters and the like can easily be obtained by reacting a 5-substituted picolinic acid represented by the formula (II):

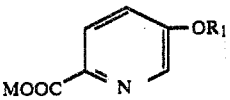
(II)

wherein $R_1$ and M are as defined above, with the corresponding aliphatic alcohol having 1 to 6 carbon atoms in the presence of an acid catalyst such as hydrochloric acid, sulfuric acid, p-toluenesulfonic acid and the like at a temperature of from 40° C. to 100° C.

5-Indanyl esters, phenyl esters and substituted phenyl esters having the formula (III) can be obtained by reacting the 5-substituted picolinic acid of the formula (II) with 5-indanol, phenyl or substituted phenol (such as p-ethylphenyl, p-methylphenol, o-methylphenol and the like), respectively, in an organic solvent such as chloroform, dioxane, dimethylformamide, pyridine and the like in the presence of a condensation agent such as dicyclohexylcarbodiimide and the like.

Acyloxyalkyl esters of the 5-substituted picolinic acid such as acetoxymethyl esters, pivaloyloxymethyl esters, α-pivaloyloxyethyl esters, α-benzoyloxyethyl esters, α-(isovaleroyloxy)ethyl esters, α-(3,4,5-trimethoxybenzoyloxy)ethyl esters and the like can be prepared by reacting the 5-substituted picolinic acid of the formula (II) with an acyloxyalkyl halide represented by the formula (XII) in a solvent such as dimethylformamide, dimethyl sulfoxide and the like in the presence of a base such as pyridine, triethylamine and the like in an amount of about 1 to 1.5 mols per mol of 5-substituted picolinic acid of the formula (II). The reaction is performed at a temperature of from −20° to 80° C. for a period of from 4 to 20 hours.

Alternatively, the compound of the formula (III) can be prepared by reacting an acid halide of a 5-substituted picolinic acid represented by the formula (XIII):

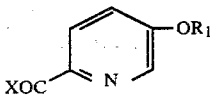
(XIII)

wherein $R_1$ is the same as defined above and X represents a halogen atom, which is obtained by reacting a 5-substituted picolinic acid represented by the formula (II) with an acid halogenating reagent, with one of an aliphatic alcohol having 1 to 6 carbon atoms, 5-indanol, phenol, substituted phenols, amines represented by the formula (XI) and acyloxyalkanols represented by the formula (XIV):

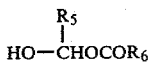
(XIV)

wherein $R_5$ and $R_6$ are the same as defined above, in the presence of a base.

5-Indanyl esters, phenyl esters and substituted phenyl esters can be obtained by reacting the acid halide of the formula (XIII) with 5-indanol, phenyl and a substituted phenol, respectively, in pyridine or in the presence of a base such as triethylamine, N,N-dimethylaniline and the like in an organic solvent such as methylene chloride, ethyl ether, dimethylformamide, dioxane and the like. Both reactions are conducted at a temperature ranging from −10° to 50° C. for a period of from 2 to 10 hours.

The acyloxyalkyl esters may also be obtained by reacting the acid halide of the formula (XIII) with an acyloxyalkanol of the formula (XIV) in an organic solvent such as methylene chloride, chloroform, dioxane, dimethylformamide and the like in the presence of a base such as triethylamine and the like or in pyridine. In this case, the reaction temperature ranges from $-30°$ to $50°$ C. and the reaction time ranges from 1 to 10 hours.

Amide derivatives of the 5-substituted picolinic acid can be prepared by reacting the 5-substituted picolinic acid of the formula (II) with an amine of the formula (XI) in an organic solvent in the presence of a condensation agent such as dicyclohexylcarbodiimide and the like or by reacting an acid halide of a 5-substituted picolinic acid of the formula (XIII) with an amine of the formula (XI) in a solvent such as methylene chloride, ethyl ether, chloroform, dioxane and the like.

Amide derivatives of the formula (III-b):

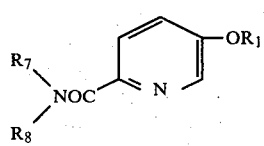

(III-b)

wherein $R_1$ is as defined above and $R_7$ and $R_8$ may be the same or different and represent a hydrogen atom, a lower alkyl group, or a phenyl group, may also be prepred by reacting the 5-substituted picolinic ester of the formula (III-a):

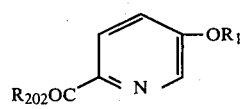

(III-a)

wherein $R_1$ is as defined above and $R_{202}$ represents a straight, branched or cyclic alkoxy group having 1 to 6 carbon atoms, an aminoalkoxy group, a phenoxy group, a substituted phenoxy group, a 5-indanyloxy group or an acyloxyalkyloxy group having the formula

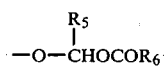

wherein $R_5$ represents a hydrogen atom or a methyl group and $R_6$ represents a lower alkyl group having 1 to 6 carbon atoms, a phenyl group or a substituted phenyl group, with an amine of the formula (XI) with or without an appropriate solvent.

This invention also provides an anti-hypertensive composition containing, as an active ingredient, a therapeutically effective amount of at least one 5-substituted picolinic acid derivative having the formula (I) described above.

The above synthesis will be illustrated in greater detail by reference to the following Examples which should not be considered as limiting the present invention. Unless otherwise indicated, all percents, parts, ratios and the like are by weight.

EXAMPLE 1

4.86 g of a potassium salt of 5-hydroxy-2-hydroxymethylpyridine was suspended in 80 ml of dimethylformamide, and 5.7 g of tetramethylene chloride and 1 g of potassium carbonate were added to the suspension, followed by stirring at 70° C. for 15 hours to effect the reaction. The reaction mixture was concentrated to dryness, and to the residue were added 150 ml each of ethyl acetate and water to form two layers. The ethyl acetate layer was separated and dried with anhydrous sodium sulfate, immediately followed by concentration to obtain 5.4 g of a syrup of 5-(4-chlorobutoxy)-2-hydroxymethylpyridine. The unreacted materials were found to remain in the aqueous layer.

4.1 g of the thus-obtained product was dissolved in a mixed solvent of 35 ml of t-butanol and 12 ml of water, and 30 ml of an aqueous solution containing 3.5 g of potassium permanganate was added dropwise thereto for 1 hour. The reaction was further continued at a temperature of 5° to 10° C. for 2 hours while stirring. The reaction mixture was filtrated, and the filter cake was washed with 50 ml of a warm 50% aqueous methanol solution (adjusted to a pH of 10 with sodium hydroxide). The filtrate and the washing were combined, the mixture was concentrated to a volume of about 30 ml, and the solvent distilled off. The resulting aqueous layer was adjusted to a pH of 1.5 with 5 N hydrochloric acid and extracted with 50 ml of chloroform. The chloroform layer was dried with anhydrous sodium sulfate and concentrated to a volume of about 3 ml. 10 ml of ethanol was then added to the concentrate, and the mixture was allowed to stand at a low temperature, and the product crystallized. The crystals thus-obtained were separated by filtration to obtain 3.5 g of white crystals of 5-(4-chlorobutoxy)picolinic acid.

Melting Point: 96°–97° C.

| Elemental Analysis for $C_{10}H_{12}N_3NCl$: | | | | |
|---|---|---|---|---|
| C | H | N | O | Cl |
| Calcd. (%): 52.29 | 5.23 | 6.10 | 29.92 | 15.47 |
| Found (%): 52.18 | 5.92 | 6.15 | | 15.32 |

EXAMPLE 2

4.3 g of a potassium salt of 5-hydroxy-2-hydroxymethylpyridine was suspended in 50 ml of dimethylsulfoxide, and 4.4 g of 1,3-dichloropropane and 500 mg of potassium carbonate were added to the suspension, followed by stirring at 60° C. for 10 hours to effect the reaction. The reaction mixture was concentrated to dryness, and 100 ml each of chloroform and water were added to the residue to form two layers. The chloroform layer was separated, dried with anhydrous sodium sulfate and immediately concentrated to dryness to obtain 4.5 g of a syrup of 5-(3-chloropropoxy)-2-hydroxymethylpyridine.

The thus-obtained product was oxidized in 50 ml of a 70% aqueous acetone with potassium permanganate in the same manner as described in Example 1 to obtain 3.7 g of white crystals of 5-(3-chloropropoxy)picolinic acid.

Melting Point: 120°–121° C.

| Elemental Analysis for $C_9H_{10}O_3NCl$: | | | | |
|---|---|---|---|---|
| C | H | N | O | Cl |
| Calcd. (%): 50.12 | 4.64 | 6.50 | 22.27 | 16.47 |
| Found (%): 50.07 | 4.72 | 6.58 | | 16.33 |

EXAMPLE 3

4.9 g of a potassium salt of 5-hydroxy-2-hydroxymethylpyridine was suspended in 90 ml of dimethylformamide, and 6.1 g of 4-bromonitrobenzene and 0.5 g of potassium carbonate were added to the suspension, and the reaction was effected at 80° C. for 18 hours. The reaction mixture was immediately concentrated to dryness, and 200 ml of chloroform and 100 ml of water were added to the residue to form two layers. The chloroform layer was separated, dried with anhydrous sodium sulfate and immediately concentrated to obtain a crystalline residue. The resulting residue was recrystallized from chloroform to obtain 5.7 g of crystals of 5-(p-nitrophenoxy)-2-hydroxymethylpyridine having a melting point of 129°–130° C.

5 g of the thus-obtained product was dissolved in 150 ml of acetone, and 80 ml of an aqueous solution containing 3.8 g of potassium permanganate was added dropwise to the solution over a 1 hour period. The reaction was further continued at room temperature for 3 hours, and the reaction mixture was filtered. The filter cake was washed with 80 ml of a warm 50% aqueous methanol (adjusted to a pH of 10 with sodium hydroxide). The filtrate and the washing were combined, concentrated to a volume of about 40 ml, adjusted to a pH of 1.5 with 5 N hydrochloric acid and extracted with 100 ml of chloroform. The extract was dried with anhydrous sodium sulfate, concentrated to a volume of about 30 ml and allowed to stand at a low temperature to crystallize the product. The thus-formed crystals were separated by filtration to obtain 4.2 g of crystals of 5-(p-nitrophenyl)picolinic acid.

Melting Point: 188°–189° C.

| Elemental Analysis for $C_{12}H_8O_5N_2$: | | | |
|---|---|---|---|
| C | H | N | O |
| Calcd. (%): 55.38 | 3.08 | 10.77 | 30.77 |
| Found (%): 55.47 | 3.12 | 10.68 | |

EXAMPLE 4

7.35 g of a potassium salt of 5-hydroxy-2-methylpyridine was suspended in 20 ml of dimethylformamide, and 9.6 g of bromochlorobenzene and 800 mg of a copper powder were added to the suspension. The reaction was effected at a temperature of 120° C. for a period of 18 hours in a nitrogen stream while stirring. After allowing the reaction mixture to cool, the reaction mixture was diluted with 50 ml of methanol and then filtered. The filtrate was immediately concentrated to dryness, and 200 ml of chloroform and 100 ml of water were added to the dried material, and the mixture adjusted to a pH of 9 with 5 N sodium hydroxide. The insoluble matter was again separated by filtration. The resulting chloroform layer was dried with anhydrous sodium sulfate and immediately concentrated to dryness to obtain 8.2 g of oily 5-(p-chlorophenoxy)-2-methylpyridine. Gas chromatography revealed that the thus-obtained product contained no 5-(p-bromophenoxy)-2-methylpyridine.

4.7 g of the above product was dissolved in 25 ml of pyridine, and 4.5 g of selenium dioxide was added to the solution, followed by stirring at 120° C. for 12 hours to effect oxidation. The reaction mixture was filtered, and the filtrate was concentrated to dryness. The concentrate was dissolved in 200 ml of chloroform and then washed successively with 100 ml of an aqueous hydrochloric acid solution at pH 2 and 50 ml of water. The chloroform layer was dried with anhydrous sodium sulfate and immediately concentrated to crystallize the product, which were then recrystallized from ethanol to obtain 4.2 g of crystals of 5-(p-chlorophenoxy)picolinic acid.

Melting Point: 158°–159.5° C.

| Elemental Analysis for $C_{12}H_8O_3NCl$: | | | | |
|---|---|---|---|---|
| C | H | N | O | Cl |
| Calcd. (%): 57.72 | 3.21 | 5.61 | 19.24 | 14.23 |
| Found (%): 57.63 | 3.26 | 5.53 | | 14.19 |

EXAMPLE 5

2.0 g of the 5-(p-chlorophenoxy)-2-methylpyridine as obtained in Example 4 was suspended in 60 ml of water, and a 1.53 g portion of potassium permanganate was added four times to the suspension while stirring at 100° C. over a 10 hour period to effect oxidation. The reaction mixture was filtered, and the filter cake washed with 30 ml of warm water. The filtrate and the washing were combined, adjusted to a pH of 9.5 with 5 N sodium hydroxide and washed with 30 ml of chloroform. The aqueous layer was adjusted to a pH of 1.5 with a 5 N aqueous hydrochloric acid solution, extracted with 50 ml of chloroform. The chloroform layer was worked up in the same manner as described in Example 4 to obtain 1.2 g of crystals of 5-(p-chlorophenoxy)picolinic acid.

EXAMPLE 6

7.4 g of a potassium salt of 5-hydroxy-2-methylpyridine, 8.5 g of p-bromotoluene and 500 mg of a copper powder were suspended in 25 ml of dimethylformamide, and the mixture was allowed to react in a nitrogen gas stream at 130° C. for 14 hours under stirring. The reaction mixture was diluted with 70 ml of methanol and filtered. The filtrate was immediately concentrated, and to the residue was added 150 ml of chloroform. The mixture was washed with 100 ml of a 0.01 N aqueous sodium hydroxide solution, whereby the unreacted 5-hydroxy-2-methylpyridine shifted to the aqueous layer. The chloroform layer was washed with water, dried with anhydrous sodium sulfate and immediately dried to obtain 8.9 g of oily 5-(p-methylphenoxy)-2-methylpyridine.

4 g of the thus-obtained product was dissolved in 20 ml of pyridine, and 4.3 g of selenium dioxide was added thereto, followed by stirring at 120° C. for 15 hours to effect oxidation. The reaction mixture was worked up in the same manner as described in Example 4 to obtain 3.1 g of crystals of 5-(p-methylphenoxy)picolinic acid.

Melting Point: 165°–166° C.

| Elemental Analysis for $C_{13}H_{11}O_3N$: | | | |
|---|---|---|---|
| C | H | N | O |
| Calcd. (%): 68.12 | 4.80 | 6.11 | 20.96 |
| Found (%): 68.17 | 4.72 | 6.19 | |

EXAMPLE 7

2.84 g of a potassium salt of 5-hydroxy-2-methylpyridine, 4.7 g of p-dibromobenzene and 400 mg of cuprous oxide were suspended in 10 ml of dimethylacetamide, and the mixture was allowed to react in a nitrogen gas stream at 150° C. for 15 hours. The reaction mixture was diluted with 30 ml of methanol and then filtered. The filtrate was immediately dried, and the residue was taken into 100 ml of chloroform and washed successively with a 3% aqueous sodium carbonate solution and 50 ml of water. The chloroform layer was dried with anhydrous sodium sulfate and immediately concentrated to dryness to obtain 2.1 g of oily 5-(p-bromophenoxy)-2-methylpyridine.

2.0 g of the thus-obtained product was then subjected to oxidation in pyridine with selenium dioxide in the same manner as described in Example 6 to obtain 1.4 g of crystals of 5-(p-bromophenoxy)picolinic acid.

Melting Point: 139°–141° C.

| Elemental Analysis for $C_{12}H_8O_3NBr$: | | | | |
|---|---|---|---|---|
| C | H | N | O | Br |
| Calcd. (%): 49.00 | 2.72 | 4.76 | 16.33 | 27.19 |
| Found (%): 49.13 | 2.64 | 4.81 | | 26.83 |

EXAMPLE 8

2.2 g of the 5-(p-nitrophenoxy)picolinic acid as obtained in Example 3 was added to a solution of 6.1 g of stannous chloride in 16.2 ml of concentrated hydrochloric acid cooled at 5° C., followed by stirring at room temperature for 16 hours. The resulting crystalline precipitate was separated by filtration and dissolved in 12 ml of warm water. To the immediately solidified crystals was added 12 ml of water, and the resulting suspension was filtered. The resulting crude crystals were washed with 25 ml of water, recrystallized from 75 ml of a mixed solvent system of concentrated hydrochloric acid/ethanol (3:5 by volume), washed with 15 ml of ethanol and dried under reduced pressure to obtain 1.0 g of colorless crystals of 5-(p-aminophenoxy)picolinic acid dihydrochloride.

Melting Point: 221°–230° C. (decomposition)

| Elemental Analysis for $C_{12}H_{10}N_2O_3 \cdot 2HCl$: | | | | |
|---|---|---|---|---|
| C | H | N | O | Cl |
| Calcd. (%): 47.52 | 3.96 | 9.24 | 15.84 | 23.43 |
| Found (%): 47.61 | 3.72 | 9.36 | | 23.40 |

EXAMPLE 9

1.4 g of the 5-(p-aminophenoxy)picolinic acid dihydrochloride as obtained in Example 8 was suspended in 22 ml of concentrated hydrochloric acid, and 3 ml of an aqueous solution containing 828 mg of sodium nitrite was added dropwise to the suspension over a period of 1 hour under ice-cooling.

5.4 ml of an aqueous solution containing 760 mg of sodium metabisulfite and 480 mg of sodium hydroxide was added to 11 ml of a warm aqueous solution containing 3.4 g of copper sulfate pentahydrate and 2.9 g of sodium chloride to prepare a cuprous chloride solution. The cuprous chloride solution was added to the diazonium salt solution as above obtained to form a solution, and 15 ml of concentrated hydrochloric acid was then added to the resulting solution, followed by stirring at 10° C. for 2 hours and then at room temperature for 16 hours to effect the reaction. The reaction mixture was diluted with 50 ml of water, adjusted to a pH of 1.5 with 5 N sodium hydroxide and extracted with 100 ml of chloroform. The extract was dried with anhydrous sodium sulfate, concentrated to a volume of about 10 ml and allowed to stand at 3° C. to form crystals, which were then separated by filtration to obtain 0.91 g of crystals of 5-(p-chlorophenoxy)picolinic acid.

EXAMPLE 10

3.68 g of a potassium salt of 5-hydroxy-2-methylpyridine was suspended in 10 ml of dimethylformamide, and 5.65 g of m-bromobenzotrifluoride and 300 mg of copper powders were added to the suspension, followed by allowing the mixture to react in a nitrogen stream at 120° C. for 15 hours while stirring. After cooling, the reaction mixture was diluted with 40 ml of acetone and filtered. The filtrate was immediately dried to solidify, and 100 ml of chloroform and 50 ml of water were added thereto. The mixture was adjusted to a pH of 9 with 5 N sodium hydroxide, and any insoluble matter was again separated by filtration. The resulting chloroform layer was dried with anhydrous sodium sulfate and immediately concentrated to dryness to obtain 4.1 g of oily 5-(m-trifluoromethylphenoxy)-2-methylpyridine.

The thus-obtained product was subjected to oxidation in pyridine using selenium dioxide in the same manner as described in Example 4. The product was crystallized from 20 ml of ethyl acetate to obtain 2.7 g of crystals of 5-(m-trifluoromethylphenoxy)picolinic acid.

Melting Point: 151°–152° C.

| Elemental Analysis for $C_{13}H_8O_3NF_3$: | | |
|---|---|---|
| C | H | N |
| Calcd. (%): 55.12 | 2.83 | 4.95 |
| Found (%): 53.68 | 2.72 | 4.79 |

EXAMPLE 11

3 g of a potassium salt of 5-hydroxy-2-methylpyridine, 3.83 g of m-bromochlorobenzene and 200 mg of a copper powder were suspended in 8 ml of dimethylformamide, followed by allowing the mixture to react in a nitrogen gas stream at 130° C. for 13 hours while stirring. The reaction mixture was diluted with 40 ml of ethanol and filtered. The filtrate was immediately concentrated, and 80 ml of chloroform was added to the residue. The mixture was washed with a 0.01 N aqueous sodium hydroxide solution. The chloroform layer was washed with water, dried with anhydrous sodium sulfate and dried to solidify to obtain 2.96 g of oily 5-(m-chlorophenoxy)-2-methylpyridine.

The thus-obtained product was subjected to oxidation using potassium permanganate in the same manner as described in Example 5 to obtain 1.43 g of crystals of 5-(m-chlorophenoxy)picolinic acid.

Melting Point: 138°–139° C.

| Elemental Analysis for $C_{12}H_8O_3NCl$: | | | |
|---|---|---|---|
| C | H | N | Cl |
| Calcd. (%): 57.72 | 3.21 | 5.61 | 14.23 |
| Found (%): 57.58 | 3.29 | 5.38 | 13.82 |

EXAMPLE 12

4 g of a potassium salt of 5-hydroxy-2-methylpyridine was suspended in 10 ml of dimethylacetamide, and 5.1 g of p-methoxybromobenzene and 450 mg of a copper powder were added to the suspension, followed by allowing the mixture to react in a nitrogen stream at 140° C. for 14 hours. The reaction mixture was diluted with 50 ml of methanol and filtered, and the filtrate was immediately dried to a solid. 100 ml of ethyl acetate was added to the residue, and the mixture was washed with 50 ml of an aqueous sodium hydroxide solution at pH 9. The ethyl acetate layer was washed with water, dried with anhydrous sodium sulfate and immediately dried to obtain 3.9 g of oily 5-(p-methoxyphenoxy)-2-methylpyridine.

The thus-obtained product was subjected to oxidation in pyridine with selenium dioxide in the same manner as described in Example 4 to obtain 1.8 g of crystals of 5-(p-methoxyphenoxy)picolinic acid.

Melting Point: 170°–172° C.

| Elemental Analysis for $C_{13}H_{11}O_4N$: | | | |
|---|---|---|---|
| | C | H | N |
| Calcd. (%): | 63.67 | 4.49 | 5.71 |
| Found (%): | 63.25 | 4.62 | 5.76 |

EXAMPLE 13

4 g of a potassium salt of 5-hydroxy-2-methylpyridine, 5.2 g of o-bromochlorobenzene and 250 mg of a copper powder were suspended in 10 ml of dimethylformamide, and the mixture was allowed to react in a nitrogen gas stream at 115° C. for 23 hours under stirring. The reaction mixture was diluted with 70 ml of methanol and filtered. The filtrate was dried to a solid, and 120 ml of chloroform was added to the residue. The mixture was washed with 70 ml of an aqueous sodium hydroxide solution at pH of 9. The solvent layer was washed with water, dried with anhydrous sodium sulfate and immediately dried to obtain 2.8 g of oily 5-(o-chlorophenoxy)-2-methylpyridine.

The thus-obtained product was subjected to oxidation in pyridine with selenium dioxide in the same manner as described in Example 4 to obtain 1.82 g of crystals of 5-(o-chlorophenoxy)picolinic acid.

Melting Point: 178°–179° C.

| Elemental Analysis for $C_{12}H_8O_3NCl$: | | | | |
|---|---|---|---|---|
| | C | H | N | Cl |
| Calcd. (%): | 57.72 | 3.21 | 5.61 | 14.23 |
| Found (%): | 57.67 | 3.15 | 5.73 | 13.82 |

EXAMPLE 14

4 g of a potassium salt of 5-hydroxy-2-methylpyridine was suspended in 10 ml of dimethylformamide, and 6.15 g of p-bromobenzotrifluoride and 500 mg of a copper powder were added to the suspension, followed by stirring in a nitrogen stream at 125° C. for 18 hours to effect the reaction. The reaction mixture was allowed to cool, diluted with 50 ml of methanol and then filtered. The filtrate was immediately dried to a solid, and 150 ml of chloroform and 100 ml of water were added to the residue. The resulting mixture was adjusted to a pH of 9.5 with 5 N sodium hydroxide and any insoluble matter again separated by filtration. The chloroform layer was dried with anhydrous sodium sulfate and immediately concentrated to dryness to obtain 5.6 g of oily 5-(p-trifluoromethylphenoxy)-2-methylpyridine.

The thus-obtained product was subjected to oxidation in pyridine with selenium dioxide in the same manner as described in Example 4 to obtain 3.8 g of crystals of 5-(p-trifluoromethylphenoxy)picolinic acid.

Melting Point: 150°–151° C.

| Elemental Analysis for $C_{13}H_8O_3NF_3$: | | | |
|---|---|---|---|
| | C | H | N |
| Calcd. (%): | 55.12 | 2.83 | 4.95 |
| Found (%): | 54.63 | 3.02 | 4.81 |

EXAMPLE 15

0.8 g of sodium hydroxide was added to a suspension of 4.63 g of 5-(3-chloropropoxy)picolinic acid in 180 ml of water, followed by stirring to obtain an aqueous solution of the sodium salt of 5-(3-chloropropoxy)picolinic acid. To this solution was added 20 ml of an aqueous solution containing 1.8 g of calcium acetate monohydrate to form a white precipitate. The thus-formed precipitate was separated by filtration, washed with water and dried over phosphorus pentoxide to obtain 4.7 g of a calcium salt of 5-(3-chloropropoxy)-picolinic acid as white powder.

Melting Point: above 220° C.

| Elemental Analysis for $C_9H_{10}O_3NCl \cdot \frac{1}{2}Ca$: | | | | |
|---|---|---|---|---|
| | C | H | N | Cl |
| Calcd. (%): | 45.86 | 4.25 | 5.94 | 15.07 |
| Found (%): | 44.72 | 4.31 | 5.73 | 14.25 |

EXAMPLE 16

8.15 g of a potassium salt of 5-hydroxy-2-hydroxymethylpyridine was suspended in 120 ml of dimethylformamide, and 10.5 g of 1,1,1-trifluoro-5-bromopentane was added to the suspension, followed by stirring at 65° C. for 18 hours to effect the reaction. The reaction mixture was immediately concentrated to dryness, and 200 ml each of chloroform and water were added to the residue to form two layers. The chloroform layer was washed with water, dried with anhydrous sodium sulfate and immediately dried to obtain 12.83 g of a syrup of 5-(5,5,5-trifluoropentyloxy)-2-hydroxymethylpyridine.

12.73 g of the thus-obtained product was dissolved in 150 ml of a mixed solvent system of t-butanol-water (3:1 by volume), and 110 ml of an aqueous solution containing 9.4 g of potassium permanganate was added dropwise thereto under ice-cooling over a period of 1.5 hours. The reaction mixture was further stirred at 10° to 20° C. for an additional 2 hour period and filtered. The filter cake was washed with 150 ml of a warm 50% aqueous methanol (adjusted to a pH 10 with sodium hydroxide). The filtrate and the washing were combined, concentrated to a volume of about 100 ml, adjusted to a pH of 1.5 with a 5 N aqueous hydrochloric acid solution and extracted with 200 ml of chloroform. The chloroform layer was dried with anhydrous sodium sulfate, concentrated to a volume of about 20 ml, mixed with 30 ml of ethanol and allowed to stand at a low temperature to form crystals, which were separated by filtration to obtain 9.1 g of white crystals of 5-(5,5,5-trifluoropentyloxy)picolinic acid.

Melting Point: 99°–101° C.

| Elemental Analysis for $C_{11}H_{12}NO_3F_3$: | | | | |
|---|---|---|---|---|
| | C | H | N | O | F |
| Calcd. (%): | 50.19 | 4.56 | 5.32 | 18.25 | 21.67 |
| Found (%): | 49.92 | 4.67 | 5.19 | | |

EXAMPLE 17

5 g of 5-(4-chlorobutoxy)picolinic acid was suspended in 30 ml of benzene, and 14 ml of thionyl chloride was added to the suspension, followed by heat-refluxing for 3 hours. The reaction mixture was immediately concentrated to dryness, and 20 ml of benzene was added to the residue. The mixture was again dried to solidify to remove the by-produced hydrogen chloride and sulfurous acid gas, thereby preparing an acid chloride of 5-(4-chlorobutoxy)picolinic acid (hydrochloride). The resulting acid chloride was dissolved in 40 ml of benzene, and the solution was added dropwise to 40 ml of a benzene solution containing 2.81 g of 5-hydroxyindane and 10.5 ml of triethylamine under ice-cooling over a period of 15 minutes while stirring. The reaction was further continued at 5° to 10° C. for 2 hours and then at room temperature for 2 hours. The reaction mixture was dried to solidify, and the residue was taken into 200 ml of chloroform. The mixture was washed successively with 50 ml each of an aqueous hydrochloric acid solution at a pH of 3, an aqueous alkali solution at a pH of 9 and distilled water. The chloroform layer was dried with anhydrous sodium sulfate, concentrated to dryness and recrystallized from a mixed solvent of ethyl ether and hexane to obtain 5.6 g of crystals of a 5-indanyl ester of 5-(4-chlorobutoxy)picolinic acid.

Melting point: 62°–63°C.

| Elemental Analysis for $C_{19}H_{20}NO_3Cl$: | | | |
|---|---|---|---|
| | C | H | N | Cl |
| Calcd. (%): | 65.99 | 5.79 | 4.05 | 10.27 |
| Found (%): | 65.28 | 5.83 | 3.97 | 10.56 |

EXAMPLE 18

1.5 g of 5-(p-chlorophenoxy)picolinic acid was dissolved in 40 ml of dried ethanol, and 0.15 ml of concentrated sulfuric acid was added to the solution, followed by heat-refluxing for 6 hours. The reaction mixture was neutralized with sodium hydrogencarbonate and concentrated to dryness. The residue was dissolved in 50 ml of chloroform and washed with 30 ml of water. The chloroform layer was decolored with a small amount of carbon powder, immediately dried to solidify, dissolved in diethyl ether and allowed to stand at a low temperature to form crystals. The thus-formed crystals were separated by filtration to obtain 1.62 g of white crystals of an ethyl ester of 5-(p-chlorophenoxy)picolinic acid.

Melting Point: 75°–76° C.

| Elemental Analysis for $C_{14}H_{12}NO_3Cl$: | | | |
|---|---|---|---|
| | C | H | N | Cl |
| Calcd. (%): | 60.54 | 4.32 | 5.05 | 12.79 |
| Found (%): | 60.42 | 4.51 | 5.13 | 13.02 |

EXAMPLE 19

14 ml of 28% aqueous ammonia was added to 30 ml of a chloroform solution containing 2.37 g of the acid chloride of 5-(o-trifluoromethylphenoxy)picolinic acid (hydrochloride), and the resulting mixture was vigorously stirred for 2 hours. The aqueous layer was removed, and the chloroform layer was washed with two 20 ml portions of water, dried with anhydrous sodium sulfate and concentrated to dryness to obtain a crystalline residue. Recrystallization from a mixed solvent system of ethanol-diethyl ether afforded 2.1 g of white crystals of 5-(o-trifluoromethylphenoxy)picolinic acid amide.

Melting Point: 137°–138° C.

| Elemental Analysis for $C_{15}H_{12}NO_3F_3$: | | | |
|---|---|---|---|
| | C | H | N | F |
| Calcd. (%): | 57.88 | 3.86 | 4.50 | 18.33 |
| Found (%): | 57.69 | 3.92 | 4.61 | |

EXAMPLE 20

1 g of 5-(p-chlorophenoxy)picolinic acid was dissolved in 20 ml of dimethylformamide, and 1.22 g of α-pivaloyloxyethyl chloride and 1.12 ml of triethylamine were added to the solution, followed by stirring at room temperature for 20 hours. 3 ml of ice-water was added to the reaction mixture, and the mixture was allowed to stand for 1 hour, followed by concentration to dryness. 70 ml of ethyl acetate was added to the residue, and the mixture was washed successively with 40 ml each of an aqueous hydrochloric acid solution at pH 3, a 5% aqueous sodium bicarbonate and water. The ethyl acetate layer was dried with anhydrous sodium sulfate, dried to solidify and dissolved in 5 ml of diethyl ether. 10 ml of hexane was added to the solution, followed by allowing the mixture to stand at a low temperature to crystallize the product. The thus-formed crystals were separated by filtration to obtain 1.2 g of white crystals of an α-pivaloyloxyethyl ester of 5-(p-chlorophenoxy)picolinic acid.

Melting Point: 120°–122° C.

| Elemental Analysis for $C_{18}H_{20}NO_5Cl$: | | | |
|---|---|---|---|
| | O | H | N | Cl |
| Calcd. (%): | 59.10 | 5.47 | 3.83 | 9.71 |
| Found (%): | 59.02 | 5.53 | 3.78 | 10.02 |

EXAMPLE 21

10 ml of a dichloromethane solution containing the acid chloride of 5-(o-chlorophenoxy)picolinic acid (hydrochloride) was added dropwise to 20 ml of a dichloromethane solution containing 0.43 g of 5-hydroxyindane and 1.6 ml of triethylamine under ice-cooling while stirring over a period of 5 minutes. The reaction was continued at 0° to 5° C. for 1 hour and then at room temperature for 2 hours. The reaction product was dried to solidify and further worked up in the same manner as described in Example 17 to obtain 1.32 g of white crystals of an indanyl ester of 5-(o-chlorophenoxy)picolinic acid.

Melting Point: 100°–102° C.

| Elemental Analysis for $C_{21}H_{16}NO_3Cl$ | | | | |
|---|---|---|---|---|
| | C | H | N | Cl |
| Calcd. (%): | 68.95 | 4.38 | 3.83 | 9.71 |
| Found (%): | 68.82 | 4.41 | 3.95 | 9.86 |

EXAMPLE 22

1.3 g of the ethyl ester of 5-(p-chlorophenoxy)picolinic acid was dissolved in 6 ml of acetone, and 15 ml of 28% aqueous ammonia was added to the solution, followed by allowing the mixture to stand at room temperature for 23 hours. The reaction mixture was cooled, and the precipitated crystals were separated by filtration and recrystallized from a mixed solvent of ethanol-diethyl ether to obtain 1.1 g of crystals of 5-(p-chlorophenoxy)picolinic acid amide.

Melting Point: 173°–174° C.

| Elemental Analysis for $C_{12}H_9N_2O_2Cl$ | | | | |
|---|---|---|---|---|
| | C | H | N | Cl |
| Calcd. (%): | 57.95 | 3.63 | 11.27 | 14.29 |
| Found (%): | 58.02 | 3.71 | 11.25 | 14.18 |

EXAMPLE 23

The composition of this Example is a tablet. A granulation was prepared of:

| | |
|---|---|
| Lactose | 65 parts |
| Corn Starch | 30 parts |
| Polyvinyl pyrrolidone | 5 parts |
| Water | A sufficient quantity |

The granulation was dried and screened. The following ingredients were then mixed well together and compressed into tablets weighing 250 mg and containing 100 mg of the calcium salt.

| | |
|---|---|
| Calcium 5-(4-chlorobutoxy)picolinate | 100 g |
| Lactose granulation | 97.5 g |
| Magnesium Stearate | 2.5 g |

EXAMPLE 24

The composition of this Example is a capsule. The following ingredients were blended and then introduced into standard clear gelatin capsules.

| | |
|---|---|
| Calcium 5-(5,5,5-trifluoropentyloxy)picolinate | 100 g |
| Lactose | 98 g |
| Magnesium Stearate | 2 g |

The resulting capsules contained 100 mg of the calcium salt per dosage unit.

All the compounds of this invention represented by the formula (I) above exhibit an anti-hypertensive activity by oral or nonoral administration and can be regarded as useful pharmaceutical agents as illustrated in the Examples 25 and 26 given below.

EXAMPLE 25

Each of the compounds of the invention as indicated below was suspended in a 5% aqueous gum arabic solution and the suspension was administered orally (100 mg/kg) to groups consisting of three spontaneously hypertensive rats (18–23 week old; blood pressure before administration: 170–190 mmHg). Blood pressure changes were determined according to a Direct Blood Pressure Measuring Method and the results obtained are shown in Table 1 below.

Each of the test compounds was administered intraperitoneally to male mice (ICR strain, 5 week old) and $LD_{50}$ value was observed 1 week after administration, and the results of acute toxicity are also shown in Table 1 below.

TABLE 1

| Test Compound | Chemical Formula | Acute Toxicity ($LD_{50}$) (mg/kg) | Maximum Depression in Blood Pressure (%) |
|---|---|---|---|
| Fusaric Acid | $C_{10}H_{13}NO_2$ | 75–100 | 15.8 |
| 5-n-Butoxy-picolinic Acid | $C_{10}H_{13}NO_3$ | 100–150 | 16.6 |
| 5-(4-Chlorobutoxy)-picolinic Acid | $C_{10}H_{12}NO_3Cl$ | 150–200 | 23.0 |
| 5-(3-Chloropropoxy)-picolinic Acid | $C_9H_{10}NO_3Cl$ | 150–200 | 18.2 |
| 5-(p-Chlorophenoxy)-picolinic Acid | $C_{12}H_8NO_3Cl$ | 150–200 | 28.3 |
| 5-(p-Methylphenoxy)-picolinic Acid | $C_{13}H_{11}NO_3$ | 200–300 | 17.0 |
| 5-(p-Aminophenoxy)-picolinic Acid Dihydrochloride | $C_{12}H_{10}N_2O_3 \cdot 2HCl$ | 450–500 | 8.3 |
| 5-(m-Trifluoromethylphenoxy)picolinic Acid | $C_{13}H_8NO_3F_3$ | 500–600 | 20.8 |
| 5-(p-Bromophenoxy)-picolinic Acid | $C_{12}H_8NO_3Br$ | 150–200 | 27.5 |
| 5-(p-Methoxyphenoxy)-picolinic Acid | $C_{13}H_{11}NO_4$ | 500–600 | 14.2 |
| 5-(m-Chlorophenoxy)-picolinic Acid | $C_{12}H_8NO_3Cl$ | 300–400 | 16.7 |
| 5-(o-Chlorophenoxy)-picolinic Acid | $C_{12}H_8NO_3Cl$ | 150–200 | 30.1 |
| 5-(p-Acetylphenoxy)-picolinic Acid | $C_{14}H_{11}NO_4$ | 400–500 | 17.3 |
| 5-(p-Trifluoromethylphenoxy)picolinic Acid | $C_{13}H_8NO_3F_3$ | 200–250 | 29.3 |
| 5-(2,4-Dimethylphenoxy)-picolinic Acid | $C_{14}H_{13}NO_3$ | 250–300 | 16.9 |
| 5-(o-Trifluoromethylphenoxy)picolinic Acid | $C_{13}H_8NO_3F_3$ | 150–200 | 27.6 |
| 5-(2,4-Dimethoxyphenoxy)-picolinic Acid | $C_{14}H_{13}NO_5$ | 400–450 | 19.2 |
| 5-(p-Nitrophenoxy)-picolinic Acid | $C_{12}H_8N_2O_5$ | 500–600 | 15.1 |
| 5-(2,6-Dichlorophenoxy)-picolinic Acid | $C_{12}H_7NO_3Cl_2$ | 150–200 | 23.7 |
| 5-(2,4-Ditrifluoromethylphenoxy)picolinic Acid | $C_{14}H_7NO_3F_6$ | 200–250 | 25.5 |
| 5-(2,4-Dichlorophenoxy)-picolinic Acid | $C_{12}H_7NO_3Cl_2$ | 150–200 | 24.6 |
| 5-(5,5,5-Trifluoropentyloxy)picolinic Acid | $C_{11}H_{12}NO_3F_3$ | 150–200 | 28.7 |
| Calcium Salt of 5-(4-Chlorobutoxy)picolinic Acid | $C_{10}H_{11}NO_3Cl \cdot \frac{1}{2}Ca$ | 800–1000 | 22.8 |
| Calcium Salt of 5-(p-Chlorophenoxy)picolinic Acid | $C_{12}H_7NO_3Cl \cdot \frac{1}{2}Ca$ | 350–400 | 23.5 |
| Calcium Salt of 5-(5,5,5-Trifluoropentyloxy)-picolinic Acid | $C_{11}H_{11}NO_3F_3 \cdot \frac{1}{2}Ca$ | 800–900 | 26.9 |

EXAMPLE 26

Each of the compounds of the invention as indicated below was suspended in a 5% aqueous gum arabic solution and the suspension was administered orally to groups consisting of three spontaneously hypertensive rats (17–23 week old; blood pressure before administration: 170–190 mmHg). Blood pressure changes were determined according to a Tail Cuff Method and the results obtained are shown in Table 2 below.

TABLE 2

| Test Compound | Dose (mg/kg) | Maximum Depression in Blood Pressure (%) |
|---|---|---|
| Indanyl Ester of 5-(4-Chlorobutoxy)-picolinic Acid | 100 | 26.3 |
| 5-(4-Chlorobutoxy)picolinic Acid Amide | 100 | 21.5 |
| Ethyl Ester of 5-(p-Chlorophenoxy)-picolinic Acid | 100 | 23.3 |
| Indanyl Ester of 5-(p-Chlorophenoxy)-picolinic Acid | 100 | 27.5 |
| α-Pivaloyloxyethyl Ester of 5-(p-Chlorophenoxy)picolinic Acid | 100 | 21.8 |
| 5-(p-Chlorophenoxy)picolinic Acid Amide | 100 | 23.7 |
| Indanyl Ester of 5-(o-Trifluoromethyl-phenoxy)picolinic Acid | 100 | 26.3 |
| 5-(o-Trifluoromethylphenoxy)picolinic Acid Amide | 100 | 20.7 |
| Indanyl Ester of 5-(o-Chlorophenoxy)-picolinic Acid | 100 | 29.0 |
| 5-(o-Chlorophenoxy)picolinic Acid Amide | 100 | 19.6 |

The oral $LD_{50}$ of free acids according to the present invention was 900 mg/kg for 5-(4-chlorobutoxy)picolinic acid and 400 to 600 mg/kg for 5-(p-chlorophenoxy)picolinic acid, 5-(o-chlorophenoxy)picolinic acid and 5-(o-trifluoromethylphenoxy)picolinic acid. On the other hand, the oral $LD_{50}$ of the indanyl esters, acyloxyalkyl esters and amide derivatives of the present invention were improved, for example, 1600–1800 mg/kg for the indanyl ester of 5-(4-chlorobutoxy)picolinic acid, 700–800 mg/kg for the indanyl ester of 5-(p-chlorophenoxy)picolinic acid, 900–1,000 mg/kg for the α-pivaloyloxyethyl ester of 5-(p-chlorophenoxy)picolinic acid, 1,500–1,600 mg/kg for 5-(4-chlorobutoxy)picolinic acid amide and 950 mg/kg for 5-(o-trifluoromethylphenoxy)picolinic acid amide.

In clinical use, the compounds of this invention may be administered orally in the form of tablets, capsules or dry syrups usually employed as vehicles. The compounds may also be administered in the form of a subcutaneous injection. In this case, derivatives having an increased water solubility, e.g., a dimethylaminoethyl ester of 5-(4-chlorobutoxy)picolinic acid hydrochloride, are suitably used.

The compounds of this invention can be used as the sole active agent or can be used in combination with one or more other physiologically active agents, particularly diuretic anti-hypertensive agents.

A dosage amount of the compounds of this invention is about 200 to about 500 mg in one or two doses per day.

While the invention has been described in detail and with reference to specific embodiments thereof, it will be apparent to one skilled in the art that varuous changes and modifications can be made therein without departing from the spirit and scope thereof.

What is claimed is:

1. 5-Substituted picolinic acids and the salts, esters and acid amides thereof represented by the formula (I):

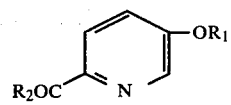

wherein $R_1$ represents a straight or branched chain halogen-substituted alkyl group having 2 to 6 carbon atoms; and $R_2$ represents an —OM group wherein M represents a hydrogen atom, a sodium atom, a potassium atom, a calcium atom, an aluminium atom or a magnesium atom, a straight or branched chain or cyclic alkoxy group having 1 to 6 carbon atoms, an aminoalkoxy group, a phenoxy group, a substituted phenoxy group, a 5-indanyloxy group, an acyloxyalkyloxy group of the formula

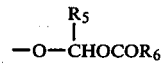

wherein $R_5$ represents a hydrogen atom or a methyl group and $R_6$ represents a lower alkyl group having 1 to 6 carbon atoms, a phenyl group or a substituted phenyl group, or an amino group represented by the formula

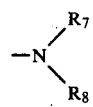

wherein $R_7$ and $R_8$, which may be the same or different, each represents a hydrogen atom, a lower alkyl group or a phenyl group.

2. The compounds of claim 1 represented by the formula (II):

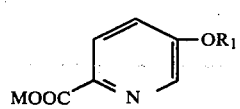

wherein $R_1$ represents a straight or branched chain halogen-substituted alkyl group having 2 to 6 carbon atoms; and M represents a hydrogen atom, a sodium atom, a potassium atom, a calcium atom, an aluminium atom or a magnesium atom.

3. The compounds of claim 1 represented by the formula (III):

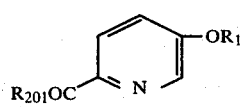

wherein $R_1$ represents a straight or branched chain halogen-substituted alkyl group having 2 to 6 carbon atoms; and $R_{201}$ represents a straight or branched chain or cyclic alkoxy group having 1 to 6 carbon atoms, an aminoalkoxy group, a phenoxy group, a substituted phenoxy group, a 5-indanyloxy group, an acyloxyalkyloxy group represented by the formula

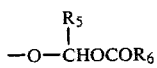

wherein $R_5$ represents a hydrogen atom or a methyl group and $R_6$ represents a lower alkyl group having 1 to 6 carbon atoms, a phenyl group or a substituted phenyl group or an amino group represented by the formula

wherein $R_7$ and $R_8$, which may be the same or different, each represents a hydrogen atom, a lower alkyl group, or a phenyl group.

4. 5-(4-Chlorobutoxy)picolinic acid and salts thereof according to claim 1.

5. 5-(3-Chloropropoxy)picolinic acid and salts thereof according to claim 1.

6. 5-(5,5,5-Trifluoropentyloxy)picolinic acid and salts thereof according to claim 1.

7. 5-(4,4,4-Trifluorobutoxy)picolinic acid and salts thereof according to claim 1.

8. An anti-hypertensive composition containing, as an active ingredient, a therapeutically effective amount of at least one 5-substituted picolinic acid, salt, ester or amide represented by the formula (I):

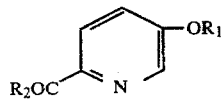

(I)

wherein $R_1$ represents a straight or branched chain halogen-substituted alkyl group having 2 to 6 carbon atoms and $R_2$ represents an —OM group wherein M represents a hydrogen atom, a sodium atom, a potassium atom, a calcium atom, an aluminium atom or a magnesium atom, a straight or branched chain or cyclic alkoxy group having 1 to 6 carbon atoms, an aminoalkoxy group, a phenoxy group, a substituted phenoxy group, a 5-indanyloxy group, an acyloxyalkyloxy group having the formula

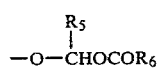

wherein $R_5$ represents a hydrogen atom or a methyl group and $R_6$ represents a lower alkyl group having 1 to 6 carbon atoms, a phenyl group or a substituted phenyl group, or an amino group having the formula

wherein $R_7$ and $R_8$, which may be the same or different, each represents a hydrogen atom, a lower alkyl group, or a phenyl group.

9. The anti-hypertensive composition of claim 8 containing, as an active ingredient, a therapeutically effective amount of at least one 5-substituted picolinic acid or salt thereof represented by the formula (II):

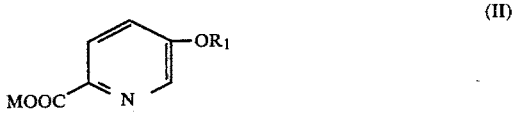

(II)

wherein $R_1$ represents a straight or branched chain halogen-substituted alkyl group having 2 to 6 carbon atoms; and M represents a hydrogen atom, a sodium atom, a potassium atom, a calcium atom, an aluminium atom or a magnesium atom.

10. The anti-hypertensive composition of claim 8 containing, as an active ingredient, a therapeutically effective amount of at least one 5-substituted picolinic ester or acid amide represented by the formula (III):

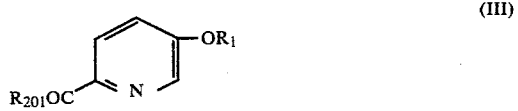

(III)

wherein $R_1$ represents a straight or branched chain halogen-substituted alkyl group having 2 to 6 carbon atoms; and $R_{201}$ represents a straight or branched chain or cyclic alkoxy group having 1 to 6 carbon atoms, an aminoalkoxy group, a phenoxy group, a substituted phenoxy group, a 5-indanyloxy group, an acyloxyalkyloxy group represented by the formula

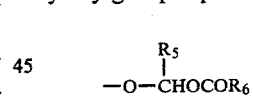

wherein $R_5$ represents a hydrogen atom or a methyl group and $R_6$ represents a lower alkyl group having 1 to 6 carbon atoms, a phenyl group or a substituted phenyl group or an amino group represented by the formula

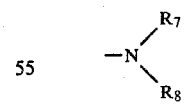

wherein $R_7$ and $R_8$, which may be the same or different, each represents a hydrogen atom, a lower alkyl group or a phenyl group.

* * * * *